(12) United States Patent
Yu et al.

(10) Patent No.: US 6,827,942 B2
(45) Date of Patent: Dec. 7, 2004

(54) COMPOSITION AND METHOD OF USE

(75) Inventors: Shiguang Yu, Topeka, KS (US); Karen Wedekind, Meriden, KS (US)

(73) Assignee: Colgate-Palmolive Co., New York, NY (US)

( * ) Notice: Subject to any disclaimer, the term of this patent is extended or adjusted under 35 U.S.C. 154(b) by 34 days.

(21) Appl. No.: 09/729,028

(22) Filed: Dec. 4, 2000

(65) Prior Publication Data

US 2002/0068766 A1 Jun. 6, 2002

(51) Int. Cl.$^7$ .............. A61K 7/06; A61K 7/00; A61K 31/045; C07C 31/04; C07C 31/08
(52) U.S. Cl. .............. 424/401; 424/402; 514/947; 514/227.2; 514/44; 514/762; 514/880; 604/19
(58) Field of Search .............. 424/401, 402; 514/947, 227.2, 44, 762, 880; 604/19

(56) References Cited

U.S. PATENT DOCUMENTS

| | | | |
|---|---|---|---|
| 4,775,361 A | * | 10/1988 | Jacques et al. ............ 604/20 |
| 4,849,455 A | | 7/1989 | Eggers et al. |
| 4,871,839 A | * | 10/1989 | Gibson ............ 536/55.1 |
| 5,344,651 A | * | 9/1994 | Schwen et al. ............ 424/402 |
| H001480 H | * | 9/1995 | Luo ............ 424/400 |
| 5,674,497 A | | 10/1997 | Kuwana et al. |
| 6,043,287 A | | 3/2000 | Nakamura |

FOREIGN PATENT DOCUMENTS

| | | | | |
|---|---|---|---|---|
| EP | 0692192 | 1/1996 | ...... | A01N/35/02 |
| EP | 0839515 | 5/1998 | ...... | A61K/7/06 |

OTHER PUBLICATIONS

The Merck Veterinary Manual, A Handbook of Diagnosis and Therapy for the Veterinarian, 1973, Merck & Co., Inc., Fourth Edition, pp. 915–916 and 1520.*

* cited by examiner

Primary Examiner—Frederick Krass
Assistant Examiner—Clinton T. Ostrup
(74) Attorney, Agent, or Firm—Martin B. Barancik

(57) ABSTRACT

A liquid composition comprising an alcohol or mixture thereof in sufficient quantity to grow hair in an area of canine or feline skin wherein alopecia has occurred.

10 Claims, No Drawings

COMPOSITION AND METHOD OF USE

BACKGROUND OF THE INVENTION

Mammal hair or fur grows in cycles and goes through three phases: anagen, catagen and telogen. In the anagen phase, hair is actively and continuously growing. Afterwards, hair goes through a short period of growth recess (catagen) and enters into telogen in which hair stops growing. The control of the hair growth cycle in mammals is poorly understood. Under normal conditions, it is predominantly controlled by photoperiod. For example, dogs and cats in northern United States shed mainly in spring and fall. Other factors such as genetics, nutrition, and hormones may also affect hair growth cycle.

Alopecia is an abnormal condition in mammals. It is defined as an absence of hair from areas of skin where hair normally is present. It could be due to loss of hair follicles or an abnormally extended telogen period after alopecia in the affected area. In the case of canine and feline, some alopecia are congenital and hereditary while others are caused by various abnormal conditions. The former can be seen in canine color mutant alopecia, feline alopecia universalis, pattern baldness of dachshund, etc. and the latter are generally called acquired alopecias such as canine and feline pinal alopecia, preauricular feline alopecia, anagen telogen defluxion, feline symmetric alopecia, and post-clipping alopecia.

Post-clipping alopecia is commonly seen in veterinary practice. Post-clipping alopecia can last for as long as 6 to 12 months after initial hair clipping. From time to time hair has to be removed or clipped, for example, prior to an operation the canine will be clipped along the area of incision so as to provide a clear field for the surgeon. Treatment of a skin condition oftentimes requires the clipping of hair around the affected area. Other occasions of clipping include venipuncture for drawing blood or injecting medicine. In each of these situations there is a need to have hair growth occur in a rapid and nonselective manner. This will provide a smoothly integrated coat in as short a time as possible.

It has now been found that hair growth can be rapidly accelerated through the application of an alcoholic composition to the surface of the dog's skin. This appears to bring about a more rapid passage of hair growth from the telogenic stage to the anagenic stage or stimulating hair growth rate or both.

SUMMARY OF THE INVENTION

In accordance with the invention there is a liquid composition comprising an alcohol or mixture thereof in sufficient quantity to grow hair in an area of a canine or feline skin wherein alopecia has occurred.

Another aspect of the invention is a method for growing hair on the skin of a canine or feline following alopecia which comprises applying to the skin of the said dog the composition of the invention in quantities and frequency sufficient to grow hair following the said alopecia.

DETAILED DESCRIPTION OF THE INVENTION

The alcohol(s) can be applied to the skin directly, or through contacting the skin with materials having absorbed alcohol such as cotton, gauze, sponge and cloth or through a vehicle used to deliver the alcohols to the skin surface. The vehicle is any liquid that solubilizes or emulsifies the alcohol(s), is easily spreadable on the skin and provides enough absorption of the alcohol(s) so as to provide the hair growing effect.

The alcohols can be used alone or in mixtures, applying directly to the canine or feline skin together with a vehicle or contacting material as mentioned previously. Such alcohol includes mono or polyalcohols such as methanol, ethanol, isopropanol, propanol, butanol, ethylene glycol, propylene glycol, glycerin, polyethylene glycol, polypropylene glycols, ethylhexane diol, hexylene glycols, and the like, a blend of ethylalcohol with varying amounts of other water soluble alcohols, particularly methanol and isopropanol, or a mixture of methanol and isopropanol. Generally ethanol is a major portion by volume. A particularly desirable group of alcohols is ethanol with methanol and/or isopropanol. Generally about 75 to about 98 vol. % ethanol with the remainder being methanol and/or isopropanol is particularly desirable with about 80 to about 94 vol. % ethanol and about 6 to about 20 vol. % methanol and/or isopropanol, preferably the mixture of methanol and isopropanol being even more desirable. Quantities of specific alcohol(s) employed as well as frequency of use is dependent upon toxicity to the animal.

The quantity of alcohol(s) applied to the skin surface is that quantity of alcohol(s) which bring about a more rapid hair growth in comparison to non-treated skin. Generally, the treated skin should be fully covered with the alcohol or the alcohol mixture for a sufficient length of time, e.g., about 2 minutes. Removal of stratum corneum using materials such as D-Square sampling disc in the treated area before alcohol treatment can facilitate the penetration of the alcohol into the skin. The frequency of application can be once or twice every two to four weeks for up to six to nine months. The alcoholic treated skin appears to take hair from the telogenic stage of essentially nongrowth to the anagenic stage of growth or brings about more rapid hair growth.

A further use of the invention is as an animal model for studying the regulation of hair growth cycle in mammals through bringing hair growth into different growth phases, i.e., anagen, catagen or telogen, in a controlled manner.

EXAMPLES

Below are examples of the invention showing the effect of the treatment on canine skin relative to untreated canine skin.

Example 1

The alcohol mixture contained ethyl alcohol (90%), methyl alcohol (5%) and isopropyl alcohol (5%).

The affected skin was first stripped 36 times with D-Squame sampling discs (a skin sampling disc made by CuDerm Corp., Dallas, Tex.); each time with a new disc. A glass ring (id=1¼ inch, height=¾ inch) was placed on the stripped area and was firmly pressed to the skin so that the alcohol mixture would not leak out. Two milliliters of the alcohol mixture was added into the glass ring. The mixture in the glass ring was gently stirred with a glass rod for 2 minutes. Then, the alcohol mixture was removed by aspiration using a pipette. The alcohol mixture treatment was repeated once, i.e., applying 2 milliliter alcohol mixture to the skin, stirring for 2 minutes, and removing the mixture with a pipette. Afterwards, Panolog Cream® was applied on the treated area. Panolog Cream® is a commercial product used in veterinary medicine to treat skin lesions. It contains nystatin, neomycin sulfate, thiostrepton and triamcinolone acetonide in the base mixture. Using Panolog Cream® alone in the affected area did not induce hair re-growth in dogs.

Thirty-six Beagles were treated with the method described above. They were treated six times in total, once every four weeks. Twenty-eight dogs showed positive response in that hair regrew in the treated area. The hair re-growth occurred only in the alcohol mixture treated area but not in the adjacent area in some dogs. In other dogs, hair was longer in the treated area than those in the adjacent area, indicating the hair in the treated area were either entering into anagen earlier and/or had a greater hair growth rate. Neither tape stripping alone nor Panolog Cream® alone caused hair re-growth when used without alcohol treatment.

What is claimed is:

1. A method for accelerating growing hair on the skin of a canine or feline having alopecia which comprises applying to the skin of said canine or feline wherein alopecia has occurred the sole active hair growth agent consisting of a mixture of at least three alcohols selected from the group consisting of methanol, ethanol, isopropanol, and propanol in sufficient quantity to accelerate hair growth in the area wherein alopecia has occurred.

2. The method of claim 1 wherein alopecia has occurred on a feline.

3. The method of claim 1 wherein alopecia has occurred in a canine.

4. The method of claim 3 wherein the canine alopecia has occurred after the hair has been clipped.

5. The method of claim 3 wherein the mixture of alcohols contains ethanol.

6. The method of claim 3 wherein the mixture of alcohols comprises as the alcohols present therein about 80 to about 94 vol. % of ethanol and about 6 to 20 vol. % of methanol, isopropanol or a mixture thereof.

7. The method of claim 3 wherein a portion of the stratum corneum of the skin wherein alopecia has occurred has been removed prior to application of the mixture of alcohols.

8. A method for accelerating growing hair on the skin of a canine or feline having alopecia wherein alopecia has occurred after the hair has been clipped which comprises applying to the skin of said canine or feline wherein alopecia has occurred the sole active hair growth agent consisting of a mixture of at least three alcohols, selected from the group consisting of methanol, ethanol, isopropanol, and propanol in sufficient quantity to accelerate hair growth in the area wherein alopecia has occurred.

9. A method for accelerating growing hair on the skin of a canine or feline having alopecia which comprises applying to the skin of said canine or feline wherein alopecia has occurred a mixture of alcohols as the sole active hair growth agent in sufficient quantity to accelerate in the area wherein alopecia has occurred, and wherein the, mixture of alcohols comprises as to the alcohols therein about 80 to about 94 vol. % ethanol and about 6 to about 20 vol. % of methanol, isopropanol and mixtures thereof.

10. A method for accelerating growing hair on the skin of a canine or feline having alopecia which comprises applying to the skin of said canine or feline wherein alopecia has occurred the sole active hair growth agent consisting of a mixture of at least three alcohols selected from the group consisting of methanol, ethanol, isopropanol, and propanol in sufficient quantity to grow hair in the area wherein alopecia has occurred and wherein a portion of the stratum corneum of the skin wherein alopecia has occurred has been removed prior to application of the mixture of alcohols.

* * * * *